(12) United States Patent
Baylink et al.

(10) Patent No.: US 8,722,399 B1
(45) Date of Patent: *May 13, 2014

(54) AGENTS AND METHOD FOR TREATING INFLAMMATION-RELATED CONDITIONS AND DISEASES

(71) Applicant: Loma Linda University, Loma Linda, CA (US)

(72) Inventors: David J. Baylink, Redlands, CA (US); Kin-Hing William Lau, Redlands, CA (US); Xuezhong Qin, Loma Linda, CA (US)

(73) Assignee: Loma Linda University, Loma Linda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/163,933

(22) Filed: Jan. 24, 2014

Related U.S. Application Data

(60) Continuation of application No. 14/076,055, filed on Nov. 8, 2013, now Pat. No. 8,669,104, which is a division of application No. 13/766,733, filed on Feb. 13, 2013, now Pat. No. 8,647,616.

(60) Provisional application No. 61/598,861, filed on Feb. 14, 2012.

(51) Int. Cl.
*C12N 5/00* (2006.01)
*C12N 5/02* (2006.01)

(52) U.S. Cl.
USPC ............................ 435/325; 435/360; 435/362

(58) Field of Classification Search
None
See application file for complete search history.

(56) References Cited

U.S. PATENT DOCUMENTS

| | | | |
|---|---|---|---|
| 6,274,359 B1 | 8/2001 | Anazawa et al. | |
| 2010/0003272 A1 | 1/2010 | Sieweke | |
| 2014/0065157 A1* | 3/2014 | Baylink et al. ............. | 424/141.1 |

FOREIGN PATENT DOCUMENTS

EP    WO2010/125115 A1    11/2010

OTHER PUBLICATIONS

Burke et al., "Macrophages in gene therapy: cellular delivery vehicles and in vivo targets," Journal of Leukocyte Biology, vol. 72: pp. 417-428, Sep. 2001, entire document.
Wang et al., "Macrophages in Renal Disease," Journal of Am. Soc. Nephrol., 22: pp. 21-27, 2011, entire document.
Loma Linda University et al., International Search Report and Written Opinion of the International Searching Authority, issued in corresponding International Patent Application No. PCT/US2013/025986 on Apr. 26, 2013.
Laurence et al., Nature Immunol., 2007, v.9, pp. 903-905.
Mestas et al., J. of Immunology, 2004, 172, pp. 2731-238.
Shanks et al., Philosophy, Ethics and Humanities in Medicine, 2009, v.4, pp. 1-20.
Baylink et al., Office Action dated Sep. 4, 2013, issued in parent U.S. Appl. No. 13/766,733.
Loma Linda University, International Preliminary Report on Patentability, issued in corresponding International Patent Application No. PCT/US2013/025986 on Jan. 14, 2014.

* cited by examiner

*Primary Examiner* — Michail Belyavskyi
(74) *Attorney, Agent, or Firm* — David A. Farah; Sheldon Mak & Anderson PC

(57) ABSTRACT

Gene-modified, inflammation-specific monocytes that comprise a 1-alpha-hydroxylase gene, where the 1-alpha-hydroxylase gene is expressed to produce functional 1-alpha-hydroxylase enzyme when the monocytes transdifferentiate into gene-modified, inflammation-specific macrophages. Gene-modified, inflammation-specific macrophages that comprise a 1-alpha-hydroxylase gene. A method for treating one or more than one inflammation-related condition or disease, the method comprising administering gene-modified, inflammation-specific monocytes that comprise a 1-alpha-hydroxylase gene, where the 1-alpha-hydroxylase gene is expressed to produce functional 1-alpha-hydroxylase enzyme when the monocytes transdifferentiate into gene-modified, inflammation-specific macrophages.

31 Claims, No Drawings

AGENTS AND METHOD FOR TREATING INFLAMMATION-RELATED CONDITIONS AND DISEASES

CROSS-REFERENCE TO RELATED APPLICATION SECTION

The present application is a continuation of U.S. patent application Ser. No. 14/076,055 titled "Agents and Method for Treating Inflammation-Related Condition and Diseases," filed Nov. 8, 2013 which is a divisional of U.S. patent application Ser. No. 13/766,733 titled "Agents and Method for Treating Inflammation-Related Conditions and Diseases" filed Feb. 13, 2013 which claims the benefit of U.S. Provisional Patent Application No. 61/598,861 entitled "Methods and Substances for Treating Inflammation," filed Feb. 14, 2012, the contents of which are incorporated in this disclosure by reference in their entirety.

STATEMENT REGARDING FEDERALLY SPONSORED RESEARCH OR DEVELOPMENT

This invention was made with United States Government support under Cooperative Agreement Number W81XWH-11-2-0052 from United States Department of Defense. The United States Government has certain rights in this invention.

BACKGROUND

Inflammation is the usual initial response of the body to harmful stimuli and is necessary for the healing of most diseases and conditions. Both the initiation of inflammation and the cessation of inflammation are complex processes. It is now known that many human conditions and diseases are caused by the inappropriate initiation of inflammation or the inappropriate lack of cessation of inflammation. Among these 'inflammation-related conditions and diseases' are sepsis and polytrauma, both of which involve simultaneous inflammation of many body tissues or organs, inflammatory neurodegenerative diseases such as Alzheimer's disease, and autoimmune diseases, such as for example antiphospholipid syndrome, atherosclerosis, autoimmune encephalomyelitis, autoimmune hepatitis, celiac disease, Graves' disease, inflammatory bowel disease (Crohn's disease and ulcerative colitis), multiple sclerosis, myasthenia gravis, myositis, polymyositis, Raynaud's phenomenon, rheumatoid arthritis, scleroderma, Sjogren's syndrome, systemic lupus, type 1 diabetes and uveitis, which involve inflammation limited to specific body tissues or organs.

Treatment of inflammation-related conditions and diseases include the administration of therapeutic agents to reduce or cease inflammation, such as anti-inflammatory agents (including 5-aminosalicylates and corticosteroids), biological drugs (including infliximab and vizilizumab) and immunosuppressants (including azathioprine, cyclosporine and mercaptopurine). Disadvantageously, however, these therapeutic agents can have severe side effects including increased risks for infectious diseases, malignancies and osteoporosis. Further, many patients do not respond to these therapeutic agents. Additionally, many of these therapeutic agents do not provide long term efficacy.

One therapeutic agent known to be effective in the treatment of inflammation-related conditions and diseases is calcitriol, the active form of vitamin D that is partially responsible for the regulation of calcium levels in humans. While the systemic administration of calcitriol has been shown to be effective in treatment of various autoimmune inflammation-related conditions and diseases in animal models, disadvantageously, the dosage of calcitriol needed to be effective was high enough to cause hypercalcemia in the treated animal limiting the potential use of calcitriol as a therapeutic agent. Further, there is evidence that deficient levels of calcitriol is a significant factor to the pathogenesis of sepsis in that there is evidence that an impairment of the production of calcitriol is associated with low serum calcium and high parathyroid hormone, and there is evidence polytrauma is frequently associated with hypocalcemia and increasing parathyroid hormone, which could also be related to impaired vitamin D metabolism.

Therefore, there is a need for a new method for treating inflammation-related conditions and diseases which is not associated with these disadvantages.

SUMMARY

According to one embodiment, there is provided gene-modified, inflammation-specific monocytes suitable for treating one or more than one inflammation-related condition or disease; the gene-modified, inflammation-specific monocytes comprising a 1-alpha-hydroxylase gene that produces functional 1-alpha-hydroxylase when the gene-modified, inflammation-specific monocytes transdifferentiate into gene-modified, inflammation-specific macrophages. In one embodiment, the 1-alpha-hydroxylase gene is a human 1-alpha-hydroxylase gene. In one embodiment, the 1-alpha-hydroxylase gene is on plasmid DNA. In another embodiment, the 1-alpha-hydroxylase gene is on a viral vector. In one embodiment, the gene-modified, inflammation-specific monocytes further comprise a growth factor gene that produces functional growth factor when the gene-modified, inflammation-specific monocytes transdifferentiate into gene-modified, inflammation-specific macrophages. In one embodiment, the growth factor gene is a human growth factor gene. In one embodiment, the growth factor gene is on plasmid DNA. In another embodiment, the growth factor gene is on a viral vector. In another embodiment, the growth factor gene is selected from the group consisting of insulin-like growth factor 1 and a transforming growth factor beta gene. In one embodiment, the gene-modified, inflammation-specific monocytes further comprise a macrophage-specific promoter that limits expression of the 1-alpha-hydroxylase gene until the gene-modified, inflammation-specific monocytes transdifferentiate into gene-modified, inflammation-specific macrophages. In one embodiment, the macrophage-specific promoter is selected from the group consisting of CD11b, CD14, c-fms, Lysozyme M and Scavenger Receptor Class A. In one embodiment, the gene-modified, inflammation-specific monocytes further comprise both a growth factor gene that produces functional growth factor when the gene-modified, inflammation-specific monocytes transdifferentiate into gene-modified, inflammation-specific macrophages, and a macrophage-specific promoter that limits expression of the 1-alpha-hydroxylase gene until the gene-modified, inflammation-specific monocytes transdifferentiate into gene-modified, inflammation-specific macrophages. In one embodiment, the gene-modified, inflammation-specific monocytes are CD14-positive and CD16-negative monocytes.

According to another embodiment of the present invention, there is provided gene-modified, inflammation-specific macrophages suitable for treating one or more than one inflammation-related condition or disease; the gene-modified, inflammation-specific macrophages comprising a 1-alpha-hydroxylase gene that produces functional 1-alpha-hydroxylase. In one embodiment, the 1-alpha-hydroxylase gene is a human 1-alpha-hydroxylase gene. In one embodiment, the 1-alpha-hydroxylase gene is on plasmid DNA. In another embodiment, the 1-alpha-hydroxylase gene is on a viral vector. In one embodiment, the gene-modified, inflammation-specific monocytes further comprise a growth factor gene that produces functional growth factor when the gene-modified, inflammation-specific monocytes transdifferentiate into gene-modified, inflammation-specific macrophages. In one embodiment, the growth factor gene is a human growth factor gene. In one embodiment, the growth factor gene is on plasmid DNA. In another embodiment, the growth factor gene is on a viral vector. In one embodiment, the growth factor gene is selected from the group consisting of insulin-like growth factor 1 and a transforming growth factor beta gene. In one embodiment, the gene-modified, inflammation-specific monocytes further comprises a macrophage-specific promoter that limits expression of the 1-alpha-hydroxylase gene until the gene-modified, inflammation-specific monocytes transdifferentiate into gene-modified, inflammation-specific macrophages, where the promoter is functional under conditions of inflammation. In one embodiment, the macrophage-specific promoter is selected from the group consisting of CD11b, CD14, c-fms, Lysozyme M and Scavenger Receptor Class A CD14. In one embodiment, the gene-modified, inflammation-specific macrophages further comprises both a growth factor gene that produces functional growth factor, and a macrophage-specific promoter. In one embodiment, the gene-modified, inflammation-specific macrophages are M2 macrophages, such as for example M2 macrophages Type A, and M2 macrophages Type B. In another embodiment, the gene-modified, inflammation-specific macrophages are Gr1-positive M2 macrophages. In another embodiment, the gene-modified, inflammation-specific macrophages are Mac1-positive macrophages. In one embodiment, the gene-modified, inflammation-specific macrophages have transdifferentiated from gene-modified, inflammation-specific monocytes according to the present invention.

According to another embodiment of the present invention, there is provided a pharmaceutical suitable for treating one or more than one inflammation-related condition or disease. The pharmaceutical comprises gene-modified, inflammation-specific monocytes according to the present invention. In one embodiment, the pharmaceutical further comprises one or more than one substance selected from the group consisting of an anti-inflammatory agent, a cell growth media, an immunosuppressant, a monoclonal antibody and a preservative.

According to another embodiment of the present invention, there is provided a pharmaceutical suitable for treating one or more than one inflammation-related condition or disease. The pharmaceutical comprises gene-modified, inflammation-specific macrophages according to the present invention. In one embodiment, the pharmaceutical further comprises one or more than one substance selected from the group consisting of an anti-inflammatory agent, a cell growth media, an immunosuppressant, a monoclonal antibody and a preservative.

According to another embodiment of the present invention, there is provided a method for treating one or more than one inflammation-related condition or disease. The method comprises: a) identifying a patient with an inflammation-related condition or disease, where the inflammation-related condition or disease is caused by the inappropriate initiation of inflammation or the inappropriate lack of cessation of inflammation; b) obtaining inflammation-specific monocytes; c) producing gene-modified, inflammation-specific monocytes from the inflammation-specific monocytes, where the gene-modified, inflammation-specific monocytes comprise a 1-alpha-hydroxylase gene, where the 1-alpha-hydroxylase gene is expressed to produce functional 1-alpha-hydroxylase enzyme when the monocytes transdifferentiate into gene-modified, inflammation-specific macrophages; d) administering an amount of the gene-modified, inflammation-specific monocytes to the patient; e) allowing the gene-modified, inflammation-specific monocytes to locate and enter into the inflamed organ or tissue affected by the condition or disease; f) allowing the gene-modified, inflammation-specific monocytes to transdifferentiate into gene-modified, inflammation-specific macrophages; and g) allowing the gene-modified, inflammation-specific macrophages to produce 1-alpha-hydroxylase, where production of the 1-alpha-hydroxylase causes the localized production of calcitriol in the inflamed organ or tissue from circulating calcidiol which is present in body fluids of the patient, thereby treating the inflammation-related condition or disease by suppressing inflammation while limiting side effects from systemic hypercalcemia. In one embodiment, the patient is a human. In one embodiment, the one or more than one inflammation-related condition or disease involves simultaneous inflammation of a plurality of body tissues or organs. In another embodiment, the one or more than one inflammation-related condition or disease that involves simultaneous inflammation of a plurality of body tissues or organs is selected from the group consisting of sepsis and polytrauma. In another embodiment, the one or more than one inflammation-related condition or disease lacks an autoimmune component. In another embodiment, the one or more than one inflammation-related condition or disease that lacks an autoimmune component is selected from the group consisting of sepsis and polytrauma. In another embodiment, the one or more than one inflammation-related condition or disease involves inflammation limited to one specific body tissue or organ. In another embodiment, the one or more than one inflammation-related condition or disease is an autoimmune disease. In another embodiment, the condition or disease is selected from the group consisting of Alzheimer's disease, antiphospholipid syndrome, atherosclerosis, autoimmune encephalomyelitis, autoimmune hepatitis, celiac disease, Graves' disease, inflammatory bowel disease, multiple sclerosis, myasthenia gravis, myositis, polymyositis, Raynaud's phenomenon, rheumatoid arthritis, scleroderma, Sjogren's syndrome, systemic lupus, type 1 diabetes and uveitis. In one embodiment, identifying the patient comprises diagnosing the patient with one or more than one inflammation-related condition or disease. In one embodiment, diagnosing the patient comprises performing one or more than one of action selected from the group consisting of performing a physical examination, performing a non-invasive imaging examination, and identifying one or more than one marker for the inflammation-related condition or disease in the blood or other body fluid of the patient. In another embodiment, identifying the patient comprises consulting patient records to determine if the patient has an inflammation-related condition or disease. In one embodiment, the inflammation-specific monocytes obtained are CD14-positive and CD16-negative monocytes. In one embodiment, obtaining inflammation-specific monocytes comprises procuring embryonic stem cells and differentiating the embryonic stem cells into the inflammation-specific monocytes. In another embodiment, obtaining inflammation-specific monocytes comprises extracting a body fluid or body tissue containing inflammation-specific monocytes from the patient. In one embodiment, extracting a body fluid or body tissue containing inflammation-specific monocytes from the patient comprises obtaining venous blood from the patient by performing venipuncture on the patient and extracting the inflammation-specific monocytes from the venous blood. In another embodiment, extracting a body fluid or body tissue containing inflammation-specific monocytes from the patient comprises performing adsorptive apheresis on the blood of the patient and extracting the inflammation-specific monocytes from the blood of the patient. In another embodiment, extracting a body fluid or body tissue containing inflammation-specific monocytes from the patient comprises obtaining bone marrow from the patient by performing a bone marrow biopsy on the patient and extracting the inflammation-specific monocytes from the bone marrow of the patient. In another embodiment, extracting a body fluid or body tissue containing inflammation-specific monocytes from the patient comprises obtaining preserved cord blood of the patient and extracting the inflammation-specific monocytes from the preserved cord blood. In one embodiment, obtaining a body fluid or body tissue containing inflammation-specific monocytes comprises extracting patient-specific induced pluripotent stem cells from the patient and performing a reprogramming factors-mediated de-differentiation of stem cells from the patient and extracting the inflammation-specific monocytes from the patient-specific induced pluripotent stem cells of the patient. In one embodiment, the method further comprises purifying the inflammation-specific monocytes from the body fluid or body tissue containing inflammation-specific monocytes, after obtaining the inflammation-specific monocytes. In one embodiment, purifying the inflammation-specific monocytes comprises performing fluorescence-activated cell sorting. In another embodiment, purifying the inflammation-specific monocytes comprises performing magnetic-activated cell sorting. In another embodiment, the method further comprises expanding and storing at least some of the isolated inflammation-specific monocytes for multiple repeated infusions. In one embodiment, expanding and storing at least some of the isolated inflammation-specific monocytes comprises freezing the isolated inflammation-specific monocytes. In one embodiment, the 1-alpha-hydroxylase gene is a human 1-alpha-hydroxylase gene. In one embodiment, the 1-alpha-hydroxylase gene is on plasmid DNA. In another embodiment, the 1-alpha-hydroxylase gene is on a viral vector. In one embodiment, producing the gene-modified, inflammation-specific monocytes comprises transducing the purified inflammation-specific monocytes with the 1-alpha-hydroxylase gene. In one embodiment, transducing the purified inflammation-specific monocytes is accomplished by electroporation with one or more than one plasmid DNA or one or more than one viral vector comprising the 1-alpha-hydroxylase gene. In one embodiment, the gene-modified, inflammation-specific monocytes further comprise one or more than one growth factor gene, where the one or more than one growth factor gene is expressed to produce a functional growth factor when the gene-modified, inflammation-specific monocytes transdifferentiate into gene-modified, inflammation-specific macrophages, and where the growth factor enhances the function of the calcitriol. In one embodiment, the growth factor gene is a human growth factor gene. In one embodiment, the growth factor gene is on plasmid DNA. In another embodiment, the growth factor gene is on a viral vector. In one embodiment, the growth factor gene is selected from the group consisting of insulin-like growth factor 1 and transforming growth factor beta gene. In another embodiment, the method further comprises transducing the purified inflammation-specific monocytes with one or more than one growth factor gene. In one embodiment, producing the gene-modified, inflammation-specific monocytes comprises transducing the purified inflammation-specific monocytes with the 1-alpha-hydroxylase gene; and where transducing the purified inflammation-specific monocytes with one or more than one growth factor gene is done simultaneously with transducing the purified inflammation-specific monocytes with the 1-alpha-hydroxylase gene. In another embodiment, where producing the gene-modified, inflammation-specific monocytes comprises transducing the purified inflammation-specific monocytes with the 1-alpha-hydroxylase gene; and where transducing the purified inflammation-specific monocytes with one or more than one growth factor gene is done serially with transducing the purified inflammation-specific monocytes with the 1-alpha-hydroxylase gene. In one embodiment, transducing the purified inflammation-specific monocytes with one or more than one growth factor gene comprises using the one or more than one plasmid DNA or one or more than one viral vector comprising the one or more than one growth factor gene. In another embodiment, transducing the purified inflammation-specific monocytes with one or more than one growth factor gene is done by electroporation with the one or more than one plasmid DNA or the one or more than one viral vector, where the one or more than one plasmid DNA or the one or more than one viral vector comprises the one or more than one growth factor gene. In one embodiment, the plasmid DNA comprises both the 1-alpha-hydroxylase gene and the one or more than one growth factor gene. In another embodiment, the viral vector comprises both the 1-alpha-hydroxylase gene and the one or more than one growth factor gene. In one embodiment, the gene-modified, inflammation-specific monocytes further comprise one or more than one macrophage-specific promoter, where the one or more than one macrophage-specific promoter tends to limit the expression of the 1-alpha-hydroxylase gene to macrophages that transdifferentiate from the gene-modified, inflammation-specific monocytes, where the promoter is functional under conditions of inflammation. In one embodiment, the one or more than one macrophage-specific promoter is a human macrophage-specific promoter. In another embodiment, the one or more than one macrophage-specific promoter is on plasmid DNA. In another embodiment, the one or more than one macrophage-specific promoter is on a viral vector. In one embodiment, one or more than one of the one or more than one macrophage-specific promoter is selected from the group consisting of CD11b, CD14, c-fms, Lysozyme M and Scavenger Receptor Class A. In one embodiment, producing the gene-modified, inflammation-specific monocytes comprising the 1-alpha-hydroxylase gene and the one or more than one macrophage-specific promoter comprises transducing the purified inflammation-specific monocytes with the 1-alpha-hydroxylase gene and the one or more than one macrophage-specific promoter. In one embodiment, transducing the purified inflammation-specific monocytes with the 1-alpha-hydroxylase gene and the one or more than one macrophage-specific promoter comprises using one or more than one plasmid DNA comprising both the 1-alpha-hydroxylase gene and the one or more than one macrophage-specific promoter. In one embodiment, transducing the purified inflammation-specific monocytes with the 1-alpha-hydroxylase gene and the one or more than one macrophage-specific promoter comprises using one or more than one viral vector comprising both the 1-alpha-hydroxylase gene and the one or more than one macrophage-specific promoter. In one embodiment, administration comprises a route selected from the group consisting of intraperitoneal administration, intramuscular administration, and intravenous infusion. In another embodiment, administration comprises infusion of the gene-modified, inflammation-specific monocytes into or adjacent to the inflamed tissue or organ. In one embodiment, the amount is between one hundred thousand and one billion cells. In another embodiment, the amount is between one million and one billion cells. In another embodiment, the amount is between one million and one hundred million cells. In another embodiment, the amount is between one million and ten million cells. In one embodiment, the gene-modified, inflammation-specific macrophages comprise one or more than one growth factor gene, and the method further comprises allowing the gene-modified, inflammation-specific macrophages to produce one or more than one growth factor from the one or more than one growth factor gene.

DESCRIPTION

According to one embodiment of the present invention, there is provided gene-modified, inflammation-specific monocytes suitable for treating one or more than one inflammation-related condition or disease. According to another embodiment of the present invention, there is provided gene-modified, inflammation-specific macrophages suitable for treating one or more than one inflammation-related condition or disease. In one embodiment, the gene-modified, inflammation-specific macrophages are produced by transdifferentiation of gene-modified, inflammation-specific monocytes according to the present invention. According to another embodiment of the present invention, there is provided a pharmaceutical suitable for treating inflammation-related conditions and diseases. The pharmaceutical comprises gene-modified, inflammation-specific monocytes according to the present invention or comprises gene-modified, inflammation-specific macrophages according to the present invention. According to one embodiment of the present invention, there provided a method for treating one or more than one inflammation-related condition or disease. The method comprises generating calcitriol directly within the organ or tissue affected by the inflammation-related condition or disease by causing expression of the gene for the enzyme 1-alpha-hydroxylase, the rate-limiting step in humans for synthesizing calcitriol, to the affected organ or tissue using gene-modified, inflammation-specific monocytes that specifically home to sites of inflammation. The calcitriol that is generated suppresses the inflammation by regulating the development and function of cell types involved in producing the inflammation. In a preferred embodiment, the method comprises adoptive transfer of gene-modified, inflammation-specific monocytes that overexpress the 1-alpha-hydroxylase gene and that are controlled by a promoter that limits expression of the 1-alpha-hydroxylase gene to the inflamed organ or tissue. Generating calcitriol directly within the inflamed organ or tissue advantageously decreases the systemic side effects of direct calcitriol administration, including eliminating systemic hypercalcemia associated with present methods of systemic administration of calcitriol directly. The monocytes, macrophages, pharmaceuticals and method will now be disclosed in detail.

As used in this disclosure, except where the context requires otherwise, the term "comprise" and variations of the term, such as "comprising," "comprises" and "comprised" are not intended to exclude other additives, components, integers or steps.

As used in this disclosure, except where the context requires otherwise, the method steps disclosed are not intended to be limiting nor are they intended to indicate that each step is essential to the method or that each step must occur in the order disclosed.

As used in this disclosure, except where the context requires otherwise, "tissue" includes both one histological type of tissue, as well as a plurality of histological types of tissue forming an organ or organ system, such as for example 'pancreatic tissue,' as will be understood by those with skill in the art.

As used in this disclosure, "calcidiol" means (6R)-6-[(1R,3aR,4E,7aR)-4-[(2Z)-2-[(5S)-5-Hydroxy-2-methylidene-cyclohexylidene]ethylidene]-7a-methyl-2,3,3a,5,6,7-hexahydro-1H-inden-1-yl]-2-methyl-heptan-2-ol (also known as vitamin D2, 25-hydroxycholecalciferol; 25-hydroxyvitamin D3; 25(OH)D; 25(OH)D2; 25(OH)D3; and calcifediol, among other names.

As used in this disclosure, "calcitriol" means (1R,3S)-5-[2-[(1R,3aR,7aS)-1-[(2R)-6-hydroxy-6-methyl-heptan-2-yl]-7a-methyl-2,3,3a,5,6,7-hexahydro-1H-inden-4-ylidene]ethylidene]-4-methylidene-cyclohexane-1,3-diol (also known as vitamin D3; 1,25-dihydroxyvitamin D; 1,25-dihydroxyvitamin D2; 1,25-dihydroxyvitamin D3; 1,25-dihydroxycholecalciferol; 1,25(OH)2D; 1,25(OH)2D2; and 1,25(OH)2D3), among other names.

As used in this disclosure,"1-alpha-hydroxylase gene" encodes the enzyme 1-alpha-hydroxylase, also known under the following alternate names and forms: calcidiol 1-monooxygenase; CYPlalpha; CYP27B1; CP2B; CYP27B; cytochrome P450VD1-alpha; cytochrome p450 27B1; cytochrome P450, family 27, subfamily B, polypeptide 1; cytochrome P450 subfamily XXVIIB polypeptide 1; cytochrome P450, subfamily XXVIIB (25-hydroxyvitamin D-1-alpha-hydroxylase), polypeptide 1; cytochrome p450 27B1; cytochrome P450C1 alpha; cytochrome P450 VD1-alpha; cytochrome P450 27B1; 1alpha(OH)ase2; 25-hydroxyvitamin D-1 alpha hydroxylase, mitochondrial; 25 hydroxyvitamin D3-1-alpha hydroxylase2; 25-hydroxyvitamin D(3) 1-alpha-hydroxylase; and 25-OHD-1 alpha-hydroxylase; and VD1 hydroxylase, among other names.

As used in this disclosure, the enzyme "1-alpha-hydroxylase" catalyzes the hydroxylation of "calcidiol" to "calcitriol" which is the rate-limiting step in the production of calcitriol in humans.

As used in this disclosure, "inflammation-related" in connection with "condition or disease" or "conditions and diseases" means "caused by the inappropriate initiation of inflammation or the inappropriate lack of cessation of inflammation" rather than merely associated with inflammation.

As used in this disclosure, "inflammation-specific monocytes" are monocytes that home specifically to inflamed tissues.

As used in this disclosure, "inflammation-specific macrophages" are macrophages that home specifically to inflamed tissues.

As used in this disclosure, "GFP" means green fluorescent protein.

According to one embodiment of the present invention, there is provided gene-modified, inflammation-specific monocytes suitable for treating one or more than one inflammation-related condition or disease. The gene-modified, inflammation-specific monocytes comprise any of the gene-modified, inflammation-specific monocytes disclosed for use in the present methods. The gene-modified, inflammation-specific monocytes comprise a 1-alpha-hydroxylase gene that produces functional 1-alpha-hydroxylase when the monocytes transdifferentiate into gene-modified, inflammation-specific macrophages. In a preferred embodiment, the 1-alpha-hydroxylase gene is a human 1-alpha-hydroxylase gene. In one embodiment, the 1-alpha-hydroxylase gene is on plasmid DNA. In another embodiment, the 1-alpha-hydroxylase gene is on a viral vector. In a preferred embodiment, the gene-modified, inflammation-specific monocytes further comprise a growth factor gene that produces functional growth factor when the gene-modified, inflammation-specific monocytes transdifferentiate into gene-modified, inflammation-specific macrophages. In one embodiment, the growth factor gene is a human growth factor gene. In one embodiment, the growth factor gene is on plasmid DNA. In another embodiment, the growth factor gene is on a viral vector. In one embodiment, the growth factor gene is selected from the group consisting of insulin-like growth factor 1 (IGF-1) (also known as somatomedin C) and a transforming growth factor beta gene (TGF-β); however, other growth factor genes can be used, as will be understood by those with skill in the art with respect to this disclosure. In another preferred embodiment, the gene-modified, inflammation-specific monocytes further comprise a macrophage-specific promoter that limits expression of the 1-alpha-hydroxylase gene until the gene-modified, inflammation-specific monocytes transdifferentiate into gene-modified, inflammation-specific macrophages. In one embodiment, the macrophage-specific promoter is selected from the group consisting of CD11b (Mac-1), CD14, c-fms, Lysozyme M and Scavenger Receptor Class A (SRA). In a particularly preferred embodiment, the gene-modified, inflammation-specific monocytes comprise a 1-alpha-hydroxylase gene that produces functional 1-alpha-hydroxylase when the gene-modified, inflammation-specific monocytes transdifferentiate into gene-modified, inflammation-specific macrophages, and further comprise a growth factor gene that produces functional growth factor when the gene-modified, inflammation-specific monocytes transdifferentiate into gene-modified, inflammation-specific macrophages, and further comprises a macrophage-specific promoter that limits expression of the 1-alpha-hydroxylase gene until the gene-modified, inflammation-specific monocytes transdifferentiate into gene-modified, inflammation-specific macrophages. In one embodiment, the gene-modified, inflammation-specific monocytes are CD14-positive and CD16-negative (+CD16−; CD14+CD16−) monocytes.

According to one embodiment of the present invention, there is provided gene-modified, inflammation-specific macrophages suitable for treating one or more than one inflammation-related condition or disease. The gene-modified, inflammation-specific macrophages comprise any of the gene-modified, inflammation-specific macrophages disclosed for use in the present method. In one embodiment, the gene-modified, inflammation-specific macrophages have transdifferentiated from gene-modified, inflammation-specific monocytes according to the present invention. The gene-modified, inflammation-specific macrophages comprise a 1-alpha-hydroxylase gene that produces functional 1-alpha-hydroxylase. In a preferred embodiment, the 1-alpha-hydroxylase gene is a human 1-alpha-hydroxylase gene. In one embodiment, the 1-alpha-hydroxylase gene is on plasmid DNA. In another embodiment, the 1-alpha-hydroxylase gene is on a viral vector. In a preferred embodiment, the gene-modified, inflammation-specific macrophages further comprise a growth factor gene that produces functional growth factor. In one embodiment, the growth factor gene is a human growth factor gene. In one embodiment, the growth factor gene is on plasmid DNA. In another embodiment, the growth factor gene is on a viral vector. In one embodiment, the growth factor gene is selected from the group consisting of insulin-like growth factor 1 (IGF-1) (also known as somatomedin C) and a transforming growth factor beta gene (TGF-β); however, other growth factor genes can be used, as will be understood by those with skill in the art with respect to this disclosure. In another preferred embodiment, the gene-modified, inflammation-specific macrophages further comprise a macrophage-specific promoter that limits expression of the 1-alpha-hydroxylase gene to macrophages. In one embodiment, the macrophage-specific promoter is selected from the group consisting of CD11b (Mac-1), CD14, c-fms, Lysozyme M and Scavenger Receptor Class A (SRA) CD14. In a particularly preferred embodiment, the gene-modified, inflammation-specific macrophages comprise a 1-alpha-hydroxylase gene that produces functional 1-alpha-hydroxylase, and further comprises a growth factor gene that produces functional growth factor, and further comprises a macrophage-specific promoter. In one embodiment, the gene-modified, inflammation-specific macrophages are M2 macrophages, such as for example M2 macrophages Type A, and M2 macrophages Type B. In another embodiment, the modified M2 macrophages are Gr1-positive M2 macrophages (Gr-1+ macrophages). In another embodiment, the gene-modified, inflammation-specific macrophages are Mac1-positive macrophages (Macrophage-1 antigen macrophages; integrin alphaMbeta2 macrophages).

According to another embodiment of the present invention, there is provided a pharmaceutical suitable for treating one or more than one inflammation-related condition or disease. In one embodiment, the pharmaceutical comprises gene-modified, inflammation-specific monocytes according to the present invention. In another embodiment, the pharmaceutical comprises gene-modified, inflammation-specific macrophages according to the present invention. In another embodiment, the pharmaceutical comprises both gene-modified, inflammation-specific monocytes according to the present invention and comprises gene-modified, inflammation-specific macrophages according to the present invention. In one embodiment, the pharmaceutical comprises one or more than one substance selected from the group consisting of an anti-inflammatory agent (such as for example a 5-aminosalicylates and a corticosteroid), a cell growth media, an immunosuppressant (such as for example azathioprine, cyclosporine and mercaptopurine), a monoclonal antibody (such as for example infliximab and vizilizumab) and a preservative.

According to one embodiment of the present invention, there is provided a method for treating one or more than one inflammation-related condition or disease. The method comprises, first, identifying a patient with an inflammation-related condition or disease suitable for treatment by the present method, where the inflammation-related condition or disease is caused by the inappropriate initiation of inflammation or the inappropriate lack of cessation of inflammation. In a preferred embodiment, the patient is a human. In one embodiment, the one or more than one inflammation-related condition or disease involves simultaneous inflammation of a plurality of body tissues or organs. In a preferred embodiment, the one or more than one inflammation-related condition or disease that involves simultaneous inflammation of a plurality of body tissues or organs is selected from the group consisting of sepsis and polytrauma. In a preferred embodiment, the one or more than one inflammation-related condition or disease lacks an autoimmune component. In a preferred embodiment, the one or more than one inflammation-related condition or disease that lacks an autoimmune component is selected from the group consisting of sepsis and polytrauma. In another embodiment, the one or more than one inflammation-related condition or disease involves inflammation limited to one specific body tissue or organ. In another embodiment, the one or more than one inflammation-related condition or disease is an autoimmune disease. In a preferred embodiment, the condition or disease is selected from the group consisting of Alzheimer's disease, antiphospholipid syndrome, atherosclerosis, autoimmune encephalomyelitis, autoimmune hepatitis, celiac disease, Graves' disease, inflammatory bowel disease (Crohn's disease and ulcerative colitis), multiple sclerosis, myasthenia gravis, myositis, polymyositis, Raynaud's phenomenon, rheumatoid arthritis, scleroderma, Sjogren's syndrome, systemic lupus, type 1 diabetes and uveitis. In one embodiment, identifying the patient comprises diagnosing the patient with one or more than one inflammation-related condition or disease suitable for treatment by the present method. In one embodiment, diagnosing the patient comprises performing one or more than one of action selected from the group consisting of performing a physical examination, performing a non-invasive imaging examination (such as for example computerized tomography, magnetic resonance imaging and ultrasound), and identifying one or more than one marker for the inflammation-related condition or disease in the blood or other body fluid of the patient. In another embodiment, identifying the patient comprises consulting patient records to determine if the patient has an inflammation-related condition or disease suitable for treatment by the present method.

Next, the method comprises obtaining inflammation-specific monocytes (ISMs). Inflammation-specific monocytes home to inflamed tissue, but not to uninflammed tissue. In one embodiment, the inflammation-specific monocytes are CD14-positive and CD16-negative (+CD16−; CD14+ CD16−) monocytes. In one embodiment, obtaining inflammation-specific monocytes (ISMs) comprises procuring embryonic stem cells, such as for example by isolating embryonic stem cells from fertilized eggs, and differentiating the embryonic stem cells into the inflammation-specific monocytes, as will be understood by those with skill in the art with respect to this disclosure. In another embodiment, obtaining inflammation-specific monocytes (ISMs) comprises extracting a body fluid or body tissue containing inflammation-specific monocytes (ISMs) from the patient. In one embodiment, extracting a body fluid or body tissue containing inflammation-specific monocytes from the patient comprises obtaining venous blood from the patient by performing venipuncture on the patient and extracting the inflammation-specific monocytes from the venous blood. In another embodiment, extracting a body fluid or body tissue containing inflammation-specific monocytes from the patient comprises performing adsorptive apheresis on the blood of the patient and extracting the inflammation-specific monocytes from the blood of the patient. In another preferred embodiment, extracting a body fluid or body tissue containing inflammation-specific monocytes from the patient comprises obtaining bone marrow from the patient by performing a bone marrow biopsy on the patient and extracting the inflammation-specific monocytes from the bone marrow of the patient. In another preferred embodiment, extracting a body fluid or body tissue containing inflammation-specific monocytes from the patient comprises obtaining preserved cord blood of the patient and extracting the inflammation-specific monocytes from the preserved cord blood. In another preferred embodiment, obtaining a body fluid or body tissue containing inflammation-specific monocytes comprises extracting patient-specific induced pluripotent stem cells, such as for example blood cells or skin cells, from the patient and performing a reprogramming factors-mediated de-differentiation of stem cells from the patient and extracting the inflammation-specific monocytes from the patient-specific induced pluripotent stem cells of the patient, as will be understood by those with skill in the art with respect to this disclosure. Any other suitable method can also be used for obtaining a body fluid or body tissue containing inflammation-specific monocytes, as will be understood by those with skill in the art with respect to this disclosure.

In one embodiment, the method further comprises purifying the inflammation-specific monocytes (ISMs). In one embodiment, purifying the inflammation-specific monocytes comprises performing fluorescence-activated cell sorting. In another embodiment, purifying the inflammation-specific monocytes comprises performing magnetic-activated cell sorting.

In one embodiment, the method further comprises expanding and storing at least some of the isolated inflammation-specific monocytes for multiple repeated infusions, as will be understood by those with skill in the art with respect to this disclosure. In one embodiment, expanding and storing at least some of the isolated inflammation-specific monocytes comprises freezing the isolated inflammation-specific monocytes.

Then, the method comprises producing gene-modified, inflammation-specific monocytes from the inflammation-specific monocytes, where the gene-modified, inflammation-specific monocytes comprise a 1-alpha-hydroxylase gene, where the 1-alpha-hydroxylase gene is expressed to produce functional 1-alpha-hydroxylase enzyme when the monocytes transdifferentiate into gene-modified, inflammation-specific macrophages. In one embodiment, the 1-alpha-hydroxylase gene is a human 1-alpha-hydroxylase gene. In one embodiment, the 1-alpha-hydroxylase gene is on plasmid DNA. In another embodiment, the 1-alpha-hydroxylase gene is on a viral vector. In a preferred embodiment, producing the gene-modified, inflammation-specific monocytes comprises transducing the purified inflammation-specific monocytes with the 1-alpha-hydroxylase gene. In one embodiment, transducing the purified inflammation-specific monocytes is accomplished by electroporation with one or more than one plasmid DNA or one or more than one viral vector comprising the 1-alpha-hydroxylase gene.

In one embodiment, the gene-modified, inflammation-specific monocytes further comprise one or more than one growth factor gene, where the one or more than one growth factor gene is expressed to produce a functional growth factor when the monocytes transdifferentiate into gene-modified, inflammation-specific macrophages, and where the growth factor enhances the function of calcitriol (the product of the 1-alpha-hydroxylase gene). In one embodiment, the growth factor gene is a human growth factor gene. In one embodiment, the growth factor gene is on plasmid DNA. In another embodiment, the growth factor gene is on a viral vector. In one embodiment, the growth factor gene is selected from the group consisting of insulin-like growth factor 1 (IGF-1) (also known as somatomedin C) and transforming growth factor beta gene (TGF-β), though other growth factor genes can be used, as will be understood by those with skill in the art with respect to this disclosure. In a preferred embodiment, producing the gene-modified, inflammation-specific monocytes comprising the one or more than one growth factor gene comprises transducing the purified inflammation-specific monocytes with one or more than one growth factor gene. In one embodiment, transducing the purified inflammation-specific monocytes with one or more than one growth factor gene is done simultaneously with transducing the purified inflammation-specific monocytes with the 1-alpha-hydroxylase gene. In another embodiment, transducing the purified inflammation-specific monocytes with one or more than one growth factor gene is done serially with transducing the purified inflammation-specific monocytes with the 1-alpha-hydroxylase gene. In another embodiment, transducing the purified inflammation-specific monocytes with one or more than one growth factor gene comprises using the one or more than one plasmid DNA or one or more than one viral vector comprising the one or more than one growth factor gene. In a preferred embodiment, transducing the purified inflammation-specific monocytes with one or more than one growth factor gene is done by electroporation with the one or more than one plasmid DNA or the one or more than one viral vector, where the one or more than one plasmid DNA or the one or more than one viral vector comprises the one or more than one growth factor gene. In a preferred embodiment, the plasmid DNA comprises both the 1-alpha-hydroxylase gene and the one or more than one growth factor gene. In another preferred embodiment, the viral vector comprises both the 1-alpha-hydroxylase gene and the one or more than one growth factor gene.

In one embodiment, the gene-modified, inflammation-specific monocytes further comprise one or more than one macrophage-specific promoter, where the one or more than one macrophage-specific promoter tends to limit the expression of the 1-alpha-hydroxylase gene, and when present, the one or more than one growth factor gene, to macrophages that transdifferentiate from the gene-modified, inflammation-specific monocytes. In one embodiment, the one or more than one macrophage-specific promoter is a human macrophage-specific promoter. In one embodiment, the one or more than one macrophage-specific promoter is on plasmid DNA. In another embodiment, the one or more than one macrophage-specific promoter is on a viral vector. In one embodiment, one or more than one of the one or more than one macrophage-specific promoter is selected from the group consisting of CD11b (Mac-1), CD14, c-fms, Lysozyme M and Scavenger Receptor Class A (SRA). Other macrophage-specific promoters can also be used, as will be understood by those with skill in the art with respect to this disclosure. In a preferred embodiment, producing the gene-modified, inflammation-specific monocytes comprising the 1-alpha-hydroxylase gene and the one or more than one macrophage-specific promoter comprises transducing the purified inflammation-specific monocytes with the 1-alpha-hydroxylase gene and the one or more than one macrophage-specific promoter. In one embodiment, transducing the purified inflammation-specific monocytes with the 1-alpha-hydroxylase gene and the one or more than one macrophage-specific promoter comprises using one or more than one plasmid DNA comprising both the 1-alpha-hydroxylase gene and the one or more than one macrophage-specific promoter. In another embodiment, transducing the purified inflammation-specific monocytes with the 1-alpha-hydroxylase gene and the one or more than one macrophage-specific promoter comprises using one or more than one viral vector comprising both the 1-alpha-hydroxylase gene and the one or more than one macrophage-specific promoter.

Next, the method comprises administering an amount of the gene-modified, inflammation-specific monocytes to the patient. In one embodiment, administration comprises a route selected from the group consisting of intraperitoneal administration, intramuscular administration, and intravenous infusion. In another embodiment, administration comprises infusion of the gene-modified, inflammation-specific monocytes into or adjacent to the inflamed tissue or organ. In one embodiment, the amount is between one hundred thousand and one billion cells. In another embodiment, the amount is between one million and one billion cells. In another embodiment, the amount is between one million and one hundred million cells. In another embodiment, the amount is between one million and ten million cells.

Then, the method comprises allowing the gene-modified, inflammation-specific monocytes to locate and enter into the inflamed organ or tissue affected by the condition or disease. Next, the method comprises allowing the gene-modified, inflammation-specific monocytes to transdifferentiate into gene-modified, inflammation-specific macrophages.

Then, the method comprises allowing activation of the one or more than one macrophage-specific promoter, thereby causing the gene-modified, inflammation-specific macrophages to produce 1-alpha-hydroxylase, where production of the 1-alpha-hydroxylase causes the localized production of calcitriol in the inflamed organ or tissue from circulating calcidiol which is present in body fluids of the patient, thereby treating the inflammation-related condition or disease by suppressing inflammation while limiting side effects, especially systemic hypercalcemia. In one embodiment, the gene-modified, inflammation-specific macrophages comprise one or more than one growth factor gene, and the method further comprises allowing the gene-modified, inflammation-specific macrophages to produce one or more than one growth factor from the one or more than one growth factor gene. Production of the one or more than one growth factor acts synergistically with the localized production of calcitriol to suppress inflammation, thereby further treating the inflammation-related condition or disease. The activation of the macrophage-specific promoter to turn on the 1-alpha-hydroxylase gene, and the growth factor gene if present, occurs automatically in the affected tissue without additional intervention. Once the treatment is complete, the gene-modified, inflammation-specific macrophages undergo apoptosis leading to termination of gene expression and preventing long term side effects of the treatment.

EXAMPLE I

Demonstration of Efficacy of Agents According to the Present Invention to Produce Calcitriol In Vivo from Exogenous Calcidiol The efficacy of agents according to the present invention to produce calcitriol in vivo was demonstrated as follows. First, bicistronic lentiviral construct which was used to express human 1-alpha-hydroxylase gene (CPY) under the control of the macrophage-specific Mac1 promoter was prepared. GFP or mCherry expressed under the control of the universal PGK promoter was added to the construct to aid simultaneous monitoring of effective transduction efficiency. Then, 293T cells were transiently transfected with either Mac1-GFP-PGK-mCherry (negative control) or Mac1-CYP-PGK-GFP plasmid DNA. At 24 hours post-transfection, the 293T cells were incubated with 2.5 µM calcidiol to provide substrate for the 1-alpha-hydroxylase enzyme. After 12 hours incubation, conditioned medium was collected and calcitriol levels were measured by radioimmunoassay (RIA) after removal of binding proteins. In the presence of the substrate calcitriol, 293T cells transfected with the Mac1-CYP-PGK-GFP plasmid synthesized calcitriol at a concentration of about 16,000 pg/mL, while production of calcitriol was negligible in the absence of the substrate demonstrating that agents according to the present invention exhibited a very high capacity to synthesize calcitriol from exogenous calcidiol.

EXAMPLE II

Demonstration of Efficacy of Agents and Method According to the Present Invention The efficacy of the agents and the method according to the present invention was demonstrated as follows. First, a bone marrow transplantation approach was used to generate Gr1+ monocytes comprising a Mac1-CYP (Mac1-1-alpha-hydroxylase gene) transgene for adoptive transfer. Eight-week-old C57BL/5 (B6) female mice were subjected to gamma-irradiation (10 Gy) to ablate endogenous hematopoietic cells. Next, one million Sca1-positive hematopoietic stem cells (HSCs) were transduced with either Mac1-GFP or Mac1-CYP lentiviral vector. Then, one million of the Sca1-positive hematopoietic stem cells transduced with Mac1-GFP (the controls) or Mac1-CYP lentiviral vector were transplanted to each of the irradiated mice through injection via tail. Over 70% of monocytes isolated from the bone marrow transplants was derived from the donor Sca1+HSCs.

Four weeks after marrow transplantation, Gr1-positive monocytes were isolated from bone marrow transplants taken from the mice. Another groups of B6 recipient mice were divided into four groups, where one group was untreated (the control group), and three groups had inflammatory bowel disease induced by oral administration of dextran sodium sulfate (3% DDS in drinking water) for six days. Of the induced groups, one group was untreated, one group was treated with one million of the isolated Gr1-positive monocytes comprising Mac1-GFP transgene, the other group was treated with one million of the isolated Gr1-positive monocytes comprising Mac1-CYP transgene. The mice were sacrificed at twelve days after induction of inflammatory bowel disease.

The one-time infusion of monocytes comprising Mac1-CYP transgene nearly completely ameliorated inflammatory bowel disease as evidenced by the following: 1) mice treated with the monocytes comprising Mac1-CYP transgene not only prevented further body weight loss but essentially regained the body weight lost during the disease induction phase ending with a body weight about 95% of that of the non-induced mice; 2) all mice treated with the monocytes comprising Mac1-CYP transgene survived while 30% of untreated mice died during the test period; and 3) mice treated with the monocytes comprising Mac1-CYP transgene had increased colon length and robust regeneration of the lost colonic crypts similar to non-induced mice. Additionally, mice treated with the monocytes comprising Mac1-CYP transgene did not show a significant increase in serum calcium levels confirming the macrophage specificity of the promoter Mac1. By comparison, mice treated with the monocytes comprising Mac1-GFP moderately reduced further body weight loss during the recovery phase but did not regain the body weight already lost, and had about the same mortality rate, colonic length and mucosal damage as untreated mice.

Therefore, the agents and method according to the present invention demonstrated the high efficiency of the present invention to treat inflammatory bowel disease without the side effect of systemic hypercalcemia.

EXAMPLE III

Demonstration of Efficacy of Agents and Method According to the Present Invention The efficacy of the agents and the method according to the present invention was demonstrated as follows. First, Gr1+ monocytes were isolated from bone marrow cells of C57BL/6 mice and treated with M-CSF (100 ng/mL) for seven days to induce formation of premature M2 macrophages. These M2 monocytes stained positively for both CD11b and Gr1. These M2 macrophages were effectively transduced by the lentiviral vector in that approximately 70% of these transduced cells expressed the GFP transgene. The M2 macrophages were isolated and then were transduced with the lentiviral vector expressing either the human 1-alpha-hydroxylase gene driven by the Mac1 promoter (Mac1-CYP) or the green fluorescent protein gene driven by the Mac1 promoter (Mac1-GFP) (the control). Inflammatory bowel disease was induced in B6 mice by oral administration of dextran sodium sulfate for six days (3% DDS in drinking water). The one million of the genetically modified M2 macrophages were then injected per mouse via tail vein to each inflammatory bowel disease induced mouse at day seven. The mice were sacrificed seven days after infusion of the genetically modified M2 macrophages.

As seen with Mac1-CYP Gr1+ monocytes, Example II above, inflammatory bowel disease induced mice treated with a single infusion of Mac1-CYP M2 macrophages showed substantial repair of the severely damaged mucosa, the prevention of body weight loss and increased colon length. Further as seen with Mac1-CYP Gr1+ monocytes, Example II above, inflammatory bowel disease induced mice treated with a single infusion of Mac1-CYP M2 macrophages did not develop systemic hypercalcemia.

Therefore, the agents and method according to the present invention demonstrated the high efficiency of the present invention to treat inflammatory bowel disease without the side effect of systemic hypercalcemia.

EXAMPLE IV

Demonstration of Efficacy of Agents and Method According to the Present Invention The efficacy of the agents and the method according to the present invention was demonstrated as follows. Sca1-positive hematopoietic stem cells (HSCs) were transduced with either Mac1-CYP-PGK-GFP (Mac1-1-alpha-hydroxylase-phosphoglycerate kinase-green fluorescent protein gene) lentiviral vector or with SFFV-CYP (spleen focus-forming virus-alpha-hydroxylase gene) lentiviral vector. Eight-week old B6 recipient mice were subjected to whole body lethal gamma ray irradiation (10 Gy). Immediately after irradiation, one million of the Sca1-positive transduced hematopoietic stem cells were transplanted to each of the irradiated mice through injection via tail. Engraftment was confirmed by determining the percentage of GFP+ cells in the circulation. After full engraftment, Experimental Autoimmune Encephalomyelitis (EAE) was induced by subcutaneous injection of the myelin specific antigens (MOG) 35-55 peptide, which initiated the peripheral activation of myelin specific CD4+ T cells, which then migrated to the central nervous system and induced an immune reaction. Clinical scores that describe the relative severity of Experimental Autoimmune Encephalomyelitis were monitored on a daily basis for four weeks. Recipient mice transplanted with hematopoietic stem cells that were transduced with the Mac1-CYP-PGK-GFP lentiviral vector exhibited delayed onset of symptoms (sixteen days compared with six days) and a reduction in peak disease activity (clinical score of between 1.0 and 1.5, compared with a clinical score of between 3.0 and 3.5). Therefore, the agents and method according to the present invention demonstrated the high efficiency of the present invention to treat inflammatory bowel disease without the side effect of systemic hypercalcemia.

EXAMPLE V

Demonstration of Efficacy of Agents and Method According to the Present Invention The efficacy of the agents and the method according to the present invention was demonstrated as follows. First, specific targeting of inflamed tissues by CD11b+/Gr1+ monocytes in mice, which correspond to human CD14+CD16− monocytes, was demonstrated. Inflammatory bowel disease (IBD) was induced in 8-week-old C57BL/6 (B6) female mice by oral administration of dextran sodium sulfate (DSS) (3% in drinking water for 7 days and 1% thereafter), which is a generally accepted mouse model for human inflammatory bowel disease. At day 5, 0.1 mL of clodronate-lyposome complex was injected intravenously to reduce endogenous monocytes. At day 7, the inflammatory bowel disease mice or healthy control mice were injected intravenously with CD11b+/Gr1+ monocytes (2 million cells/mouse) isolated from green fluorescent protein (GFP) transgenic mice. Green fluorescent protein produced in these monocytes allowed localization of the position of the infused monocytes. At day 10, the mice were perfused with phosphate-buffered saline (PBS) to remove un-engrafted exogenous monocytes. Tissues were collected for detection of the green fluorescent protein marker in collected tissues and it was found that injected Gr1+ monocytes migrated only to the inflamed colon of inflammatory bowel disease mice but not to the colon of healthy mice.

Second, the agents and method according to the present invention were used to treat dextran sodium sulfate-induced inflammatory bowel disease in mice as a model for human inflammatory bowel disease to test the efficacy of the agents and method according to the present invention. CD11b+/Gr1+ monocytes were isolated from the bone marrow or blood of the mice using magnetic-activated cell sorting (CD11b+/Gr1+ monocytes correspond to human CD14+CD16− monocytes). The isolated monocytes were electroporated with either CD14-mCherry-PGK-GFP plasmid DNA or CD14-CYP27b1-PGK-GFP plasmid DNA. The electroporated monocytes were injected systemically in the inflammatory bowel disease mice. Migration of injected monocytes to inflamed colon was demonstrated by green fluorescent protein staining of colon sections upon histological examination. Severe mucosal damage and inflammatory cell infiltration occurred in the colon of the dextran sodium sulfate-treated mice. These pathologic damages were significantly reduced by intravenous injection of monocytes expressing the 1-alpha-hydroxylase gene, but not reduced by injection of monocytes expressing only a non-therapeutic marker gene.

Then, the efficacy of the agents and method according to the present invention was confirmed in an additional study. Six groups of animals were used in this study: Group 1: control healthy mice; Group 2: mice that were treated with dextran sodium sulfate to induce inflammatory bowel disease but that did not receive any therapy; Group 3: mice that were treated with dextran sodium sulfate to induce inflammatory bowel disease and that received intraperitoneal injections with calcitriol (200 ng/day/mouse) (the positive control group); Group 4: mice that were treated with dextran sodium sulfate to induce inflammatory bowel disease and that received intravenous injections with monocytes electroporated with CD14 promoter-mCherry plasmid (the negative control group); Group 5: mice that were treated with dextran sodium sulfate to induce inflammatory bowel disease and that received intravenous injections with monocytes electroporated with CD14 promoter-1-alpha-hydroxylase gene plasmid (the treatment group); Group 6: mice that were treated with dextran sodium sulfate to induce inflammatory bowel disease and that received intravenous injections with monocytes electroporated with plasmids expressing both 1-alpha-hydroxylase gene and transforming growth factor beta gene (a second treatment group). Injections were made at day 7 post-disease induction by dextran sodium sulfate. All mice were sacrificed at day 10.

At day 7 post-dextran sodium sulfate treatment, mice lost 20-25% of their body weight. In the absence of any therapeutic treatment (Group 2), these inflammatory bowel disease mice lost an additional 15-18% of their body weight by Day 8-10. About 50% of mice receiving no treatment had to be sacrificed in order to obtain blood and live tissue samples, as they were too weak to survive by Day 10. Systemic calcitriol injections failed to prevent body weight loss. While injection of monocytes expressing non-therapeutic genes (mCherry) reduced body weight loss, injection of monocytes expressing 1-alpha-hydroxylase gene alone or together with transforming growth factor beta gene was more effective in reducing weight loss. In contrast to a more than 30% increase in serum calcium in the calcitriol-treated inflammatory bowel disease mice, no hypercalcemia occurred in inflammatory bowel disease mice receiving injection of monocytes expressing 1-alpha-hydroxylase gene alone or in combination with transforming growth factor beta gene. Thus, the method for treating one or more than one inflammation-related condition or disease according to the present invention prevented body weight loss in dextran sodium sulfate mice but did not cause hypercalcemia. Injection of monocytes overexpressing non-therapeutic mCherry marker gene did not markedly reduce the severity of colon lesions. In contrast, injection of monocytes overexpressing the 1-alpha-hydroxylase gene not only prevented body weight loss but also dramatically reduced the lesion area. Systemic calcitriol injections failed to prevent body weight loss, however, it did improve colon mucosal integrity. This discrepancy is probably due to the suppression of inflammation by the high dose of calcitriol, while the severe hypercalcemia it caused led to a deterioration of the overall health of the mice. Therefore, inflammation-specific monocytes-based 1-alpha-hydroxylase gene adoptive therapy according to the present invention is highly effective in treating inflammatory bowel disease without producing a general systemic hypercalcemia.

The method for treating one or more than one inflammation-related condition or disease according to the present invention has several advantages compared with other cell-based gene therapies. First, the present method does not require prolonged ex-vivo cell culture and expansion, thereby substantially reducing the cost of the treatment. Second, based on the animal studies above, a single injection of gene-modified, inflammation-specific monocytes was sufficient to treat the disease, though the present invention includes the use of multiple doses if needed. Third, the only product of the 1-alpha-hydroxylase gene in humans is calcitriol, which is harmless to the body as long as the overexpression of calcitriol is limited to the diseased tissue preventing systemic hypercalcemia. Fourth, transduction of the monocytes with the 1-alpha-hydroxylase gene can be made by electroporation of naked plasmid DNA which does not involve the use of any viral vector for gene transfer, thereby eliminating any risk associated with the use of viral vectors, though the present method includes the use of viral vectors when warranted.

Although the present invention has been discussed in considerable detail with reference to certain preferred embodiments, other embodiments are possible. Therefore, the scope of the appended claims should not be limited to the description of preferred embodiments contained in this disclosure.

What is claimed is:

1. Gene-modified, inflammation-specific monocytes suitable for treating one or more than one inflammation-related condition or disease within inflamed tissue; the gene-modified, inflammation-specific monocytes comprising:

a) a 1-alpha-hydroxylase gene that produces functional 1-alpha-hydroxylase when the monocytes transdifferentiate into gene-modified, inflammation-specific macrophages, thereby producing calcitriol locally within the inflamed tissue; and b) a growth factor gene that produces functional growth factor locally within the inflamed tissue when the gene-modified, inflammation-specific monocytes transdifferentiate into gene-modified, inflammation-specific macrophages;

where the growth factor acts synergistically with the calcitriol to suppress inflammation, thereby treating the inflammation-related condition or disease.

2. The gene-modified, inflammation-specific monocytes of claim 1, where the 1-alpha-hydroxylase gene is a human 1-alpha-hydroxylase gene.

3. The gene-modified, inflammation-specific monocytes of claim 1, where the 1-alpha-hydroxylase gene is on plasmid DNA.

4. The gene-modified, inflammation-specific monocytes of claim 1, where the 1-alpha-hydroxylase gene is on a viral vector.

5. The gene-modified, inflammation-specific monocytes of claim 1, where the growth factor gene is a human growth factor gene.

6. The gene-modified, inflammation-specific monocytes of claim 1, where the growth factor gene is on plasmid DNA.

7. The gene-modified, inflammation-specific monocytes of claim 1, where the growth factor gene is on a viral vector.

8. The gene-modified, inflammation-specific monocytes of claim 1, where the growth factor gene is selected from the group consisting of insulin-like growth factor 1 and a transforming growth factor beta gene.

9. The gene-modified, inflammation-specific monocytes of claim 1, further comprising a macrophage-specific promoter that limits expression of the 1-alpha-hydroxylase gene until the gene-modified, inflammation-specific monocytes transdifferentiate into gene-modified, inflammation-specific macrophages, where the promoter is functional under conditions of inflammation.

10. The gene-modified, inflammation-specific monocytes of claim 9, where the macrophage-specific promoter is selected from the group consisting of CD11b, CD14, c-fms, Lysozyme M and Scavenger Receptor Class A.

11. The gene-modified, inflammation-specific monocytes of claim 1, further comprising both a growth factor gene that produces functional growth factor when the gene-modified, inflammation-specific monocytes transdifferentiate into gene-modified, inflammation-specific macrophages, and a macrophage-specific promoter that limits expression of the 1-alpha-hydroxylase gene until the gene-modified, inflammation-specific monocytes transdifferentiate into gene-modified, inflammation-specific macrophages.

12. The gene-modified, inflammation-specific monocytes of claim 1, where the gene-modified, inflammation-specific monocytes are CD14-positive and CD16-negative monocytes.

13. A pharmaceutical suitable for treating one or more than one inflammation-related condition or disease, the pharmaceutical comprising gene-modified, inflammation-specific monocytes according to claim 1.

14. The pharmaceutical according to claim 13, further comprising one or more than one substance selected from the group consisting of an anti-inflammatory agent, a cell growth media, an immunosuppressant, a monoclonal antibody and a preservative.

15. Gene-modified, inflammation-specific macrophages that have transdifferentiated from gene-modified, inflammation-specific monocytes according to claim 1.

16. Gene-modified, inflammation-specific macrophages suitable for treating one or more than one inflammation-related condition or disease within inflamed tissue; the gene-modified, inflammation-specific macrophages comprising:

a) a 1-alpha-hydroxylase gene that produces functional 1-alpha-hydroxylase, thereby producing calcitriol locally within the inflamed tissue; and b) a growth factor gene that produces functional growth factor locally within the inflamed tissue, where the growth factor acts synergistically with the calcitriol to suppress inflammation, thereby treating the inflammation-related condition or disease.

17. The gene-modified, inflammation-specific macrophages of claim 16, where the 1-alpha-hydroxylase gene is a human 1-alpha-hydroxylase gene.

18. The gene-modified, inflammation-specific macrophages of claim 16, where the 1-alpha-hydroxylase gene is on plasmid DNA.

19. The gene-modified, inflammation-specific macrophages of claim 16, where the 1-alpha-hydroxylase gene is on a viral vector.

20. The gene-modified, inflammation-specific macrophages of claim 16, where the growth factor gene is a human growth factor gene.

21. The gene-modified, inflammation-specific macrophages of claim 16, where the growth factor gene is on plasmid DNA.

22. The gene-modified, inflammation-specific macrophages of claim 16, where the growth factor gene is on a viral vector.

23. The gene-modified, inflammation-specific macrophages of claim 16, where the growth factor gene is selected from the group consisting of insulin-like growth factor 1 and a transforming growth factor beta gene.

24. The gene-modified, inflammation-specific macrophages of claim 16, further comprising a macrophage-specific promoter that limits expression of the 1-alpha-hydroxylase gene until the gene-modified, inflammation-specific macrophages transdifferentiate from gene-modified, inflammation-specific monocytes, where the promoter is functional under conditions of inflammation.

25. The gene-modified, inflammation-specific macrophages of claim 24, where the macrophage-specific promoter is selected from the group consisting of CD11b, CD14, c-fms, Lysozyme M and Scavenger Receptor Class A.

26. The gene-modified, inflammation-specific macrophages of claim 16, further comprising both a growth factor gene that produces functional growth factor, and a macrophage-specific promoter.

27. The gene-modified, inflammation-specific macrophages of claim 16, where the gene-modified, inflammation-specific macrophages are M2 macrophages.

28. The gene-modified, inflammation-specific macrophages of claim 16, where the gene-modified, inflammation-specific macrophages are Gr1-positive M2 macrophages.

29. The gene-modified, inflammation-specific macrophages of claim 16, where the gene-modified, inflammation-specific macrophages are Mac1-positive macrophages.

30. A pharmaceutical suitable for treating one or more than one inflammation-related condition or disease, the pharmaceutical comprising gene-modified, inflammation-specific macrophages according to claim 16.

31. The pharmaceutical according to claim 30, further comprising one or more than one substance selected from the group consisting of an anti-inflammatory agent, a cell growth media, an immunosuppressant, a monoclonal antibody and a preservative.

* * * * *